United States Patent
Ogle (10) Patent No.: US 6,328,869 B1
(45) Date of Patent: Dec. 11, 2001

(54) APPARATUS FOR MACROMOLECULE PURIFICATION

(75) Inventor: David Ogle, Cowan (AU)

(73) Assignee: Gradipore Limited (AU)

( * ) Notice: Subject to any disclaimer, the term of this patent is extended or adjusted under 35 U.S.C. 154(b) by 0 days.

(21) Appl. No.: 09/390,565

(22) Filed: Sep. 3, 1999

(30) Foreign Application Priority Data

Sep. 7, 1998 (AU) .................................................. PP5765

(51) Int. Cl.[7] .................................................. G02N 27/26
(52) U.S. Cl. .......................... 204/600; 204/606; 204/627
(58) Field of Search ........................... 210/321.6, 321.75, 210/321.84; 204/450, 466, 600, 616, 518, 523, 546, 627, 634, 635, 636, 638, 641

(56) References Cited

U.S. PATENT DOCUMENTS

| | | | |
|---|---|---|---|
| 3,761,386 | * 9/1973 | Smith | 204/635 |
| 3,989,613 | 11/1976 | Gritzner | 204/543 |
| 4,461,693 | * 7/1984 | Jain | 204/635 |
| 5,015,388 | * 5/1991 | Pusineri et al. | 210/641 |
| 5,039,386 | 8/1991 | Margolis | 204/466 |

FOREIGN PATENT DOCUMENTS

| | | |
|---|---|---|
| 0 369 945 A2 | 5/1990 | (EP) . |
| WO 94/22904 | 10/1994 | (WO) . |

* cited by examiner

Primary Examiner—T. Tung
Assistant Examiner—Alex Noguerola
(74) Attorney, Agent, or Firm—Arter & Hadden LLP; John X. Garred; Susan L. Mizer (57) ABSTRACT

An electrophoresis apparatus, comprises a cartridge configured to be removably mounted in the apparatus, and a separation membrane positioned in the cartridge. The separation membrane has a first side along which a first flow path defined in a first grid element and a second side along which a second flow path defined in a second grid element is provided. Restriction membranes separate buffer flow from the first flow path and the second flow path. The apparatus includes connection blocks which house electrodes and inlets and outlets for buffer flow and sample flows. The cartridge is removable from the connection blocks for replacement with another cartridge.

5 Claims, 8 Drawing Sheets

APPARATUS FOR MACROMOLECULE PURIFICATION

FIELD OF THE INVENTION

This invention relates to an apparatus for purification of macromolecules in solution and in particular to a cartridge or cassette for use in a macromolecular purification apparatus.

BACKGROUND OF THE INVENTION

European patent No 352286 relates to improvements in the separation of macromolecular solutes by a process known as electrophoretic separation, in particular fixed boundary electrophoretic separation. In fixed boundary electrophoresis, as is explained in more detail below in the description following the Brief Description of the Drawings, a semi-permeable membrane (hereinafter referred to as a separation membrane) acts to separate two streams of liquid carrying macromolecular solutes such as proteins, referred to as the upstream and the downstream. The streams pass between charged electrodes and at least one macromolecular solute migrates across the membrane from one stream to the other under the influence of the electric field. The apparatus also includes flow paths for buffer solution and further semi-permeable membranes, hereinafter referred to as restriction membranes, disposed between the electrodes and the separation membrane. The restriction membranes allow the passage of ions but not macromolecules.

The present invention relates to developments and improvements over the ideas and principals disclosed in EP 352286 and in particular to refinements and improvements to the apparatus to make the technology easier to use and operate.

In particular, it is one desired object of the present invention to provide an apparatus which is easier to fill, empty, clean and reassemble in contrast to existing apparatus such as that described above which tends to be formed substantially integrally with storage tanks, pumps, cooling apparatus and similar features making the apparatus expensive and difficult to handle and clean.

The lack of ease of use of the prior art apparatus is a serious disadvantage and tends to make separation of molecules by electrophoresis an unnecessarily complicated, tedious, time-consuming and expensive procedure.

Thus it is a further object of the present invention to provide an electrophoresis apparatus which is simpler and relatively quicker to operate than existing apparatus to set up and use.

A further problem associated with the prior art id the amount of "downtime" involved after the apparatus has been used and before it can be set up for a further separation. Electrophoresis apparatus is expensive and the downtime is consequently a serious cost disadvantage.

Thus it is a further object of the present invention to provide an apparatus whose downtime is reduced in comparison with prior art apparatus.

A yet further problem of existing electrophoresis apparatus relates to the size of the samples which are typically separated by such apparatus, the amount of sample to be separated can be very expensive, and consequently the smaller the sample which can be separated by the apparatus, the better.

It is a yet further object of the present invention to provide an apparatus which can be used to separate relatively small samples sizes.

Existing electrophoresis apparatus is also very bulky and can take up a large area of laboratory space.

It is a yet further object of the present invention to provide an apparatus which in its preferred embodiment can be relatively compact.

A further problem with existing electrophoresis apparatus is that it can require a relatively high current and voltage to operate.

It is a further object of the present invention to enable an electrophoresis apparatus which uses less power and hence is more economical and also causes less electrical heating to the sample being separated which can damage the sample.

SUMMARY OF THE INVENTION

In a first broad aspect, the present invention provides an apparatus for free flow electrophoresis in which a separation membrane, a first flow path along one side of the separation membrane, and a second flow path along an opposite side of the separation membrane and restriction membranes for separating buffer flow from the flow paths, are housed in a cartridge which can be removed from the apparatus for replacement with another cartridge, after use.

The construction of an apparatus in which the separation membrane and flow paths are defined in a removable cartridge provides a modular system which has substantial advantages of the known prior art. The need to clean, readjust, and re-set the apparatus after a separation has been carried out is reduced. The used cartridge is easily removed and a new cartridge may be simply inserted. The upstream and downstream circuits only require cleaning although the buffer may be replaced if desired.

Thus the present invention advantageously provides an apparatus whose downtime is greatly reduced in comparison with prior art apparatus. This produces substantial savings in terms of time and cost efficiency and may also enable the separation of samples at a more commercial scale than is possible with existing electrophoresis apparatus.

In one particular preferred embodiment, the apparatus includes an upper and a lower connection block which defines inlet and outlet means for feeding liquid into the first flow path (the downstream) and into the second flow path (the upstream), in the cartridge.

This arrangement enable the cartridges to be simply inserted between the two blocks and the blocks may be brought together, by a screw clamp or the like to engage the cartridge.

The upper and lower connection blocks may house electrodes and connection means for connecting the electrodes to a power source.

In one particularly preferred embodiment, the electrodes are made of titanium mesh coated with platinum.

The standard electrodes usually used for prior art electrolytic cells comprise platinum wire. The platinum coated titanium expanded mesh used in accordance with preferred embodiments of the present invention has several advantages over platinum wire in particular the ridged structure is self supporting and less expensive than platinum wire. The mesh also may provide a greater surface area and tends to allow higher currents to pass through the separation unit with less electrical power losses of the electrode. The electrodes may thus have a longer useful life.

The upper and lower connection blocks may be made of any suitable material for example a plastics material. The blocks may be transparent or opaque.

The upper and lower electrodes may be housed in recesses or channels defined in the upper and lower connection blocks, respectively. Those channels may define part of the boundaries of the buffer flow path for the apparatus. The other boundary for the buffer flow path is defined by the restriction membranes housed in the cartridge which form the upper and lower faces of the cartridge. The upper and lower connection blocks may define inlets and outlets for buffer flow.

In a related aspect the invention also encompasses a cartridge for use in the apparatus of the present invention, the cartridge including a housing and containing a separation membrane, a first flow path defined along one side of the separation membrane, and a second flow path defined along an opposite side of the separation membrane and restriction membranes for isolating buffer flow from the first and second flow paths.

The cartridge may further include gaskets positioned either side of the restriction membranes for sealing the components between the upper and lower connection blocks. The first and second flow paths may be defined by first and second grid elements. Each grid element may be generally planar and relatively thin.

The use of a relatively thin planar grid element defining the first and second flow paths may provide substantial advantages over the existing art. First, a relatively thin grid element tends to increase the liquid velocity and pressure and thus may result in a more even distribution of liquid over the separation membrane in the cartridge.

The resultant relatively higher liquid velocity may also assist in inhibiting fouling of the separation membrane.

Also, the volume of liquid required may be decreased by the use of a relatively thin grid which enables relatively smaller sample volumes to be used for laboratory separations and this may be a significant advantage over the prior art when the samples are expensive to produce.

Finally, the use of a relatively thinner grid element may enable less electrical power to be deposited into the liquid since power supplied to the liquid across the grid region, depends on the thickness of the grid. Thus, a relatively smaller power supply unit may be used, and this may make the process more economical. If less heat is transferred into the liquid the temperature of the liquid remains lower. This is advantageous since high temperatures may destroy the sample and product.

The grid element and restriction membranes may include a through hole located near each end of the element/membrane for the passage of upstream and downstream liquid therethrough to the grid element. The grid element may include a central elongate at least part cut out portion which in the assembled cartridge in conjunction with the two adjacent membranes, defines a flow path or channel from the hole one end of the grid element to the hole at the other end. The flow path may include a lattice for supporting the separation membrane and for mixing the flow.

All the elements of the cartridge apart form the cartridge housing or casing are generally planar and are assembled together in a sandwich type construction.

BRIEF DESCRIPTION OF THE DRAWINGS

The invention will now be described, by way of example only, and with reference to the accompanying drawings in which.

DETAILED DESCRIPTION OF THE PREFERRED EMBODIMENT

Before describing a preferred embodiment in detail, some of the principals of operation of an apparatus in accordance with the present invention will first be described. The description is not intended to limit the present invention to any one particular principal or theory of operation.

An electric field applied to macromolecules, such as proteins, in solution, will tend to cause the proteins to move to the electrodes. If the protein has a positive charge, it will tend to move to the negative electrode (cathode). Conversely, a negatively charged protein will tend to move to the positive electrode (anode).

In an apparatus in accordance with the present invention, a separation membrane may be placed in the electric field and molecules may be selectively transported between two circulating streams which may be called the upstream and the downstream. The particular separation membrane used may vary for different applications and may generally have a relatively large, but relatively well defined, pore size. The upstream and downstream may be isolated from the electrodes by buffer streams and by two restriction membranes. The restriction membranes may allow the movement of small molecules and ions up to a molecular weight of about 3,000 daltons.

An apparatus in accordance with the present invention may be operated in at least four different modes. Examples of those modes are set out below and are illustrated in FIGS. 1 to 4, respectively.

1. Charge based separation

In principal, any two molecules with different pIs may be separated by carrying the separation out at a pH between the two pIs. The pI is the pH of a solution in which the molecule has neutral charge, thus by changing the pH of the solution in which a molecule is present, the effective charge of that molecule may be changed.

Figure 1:
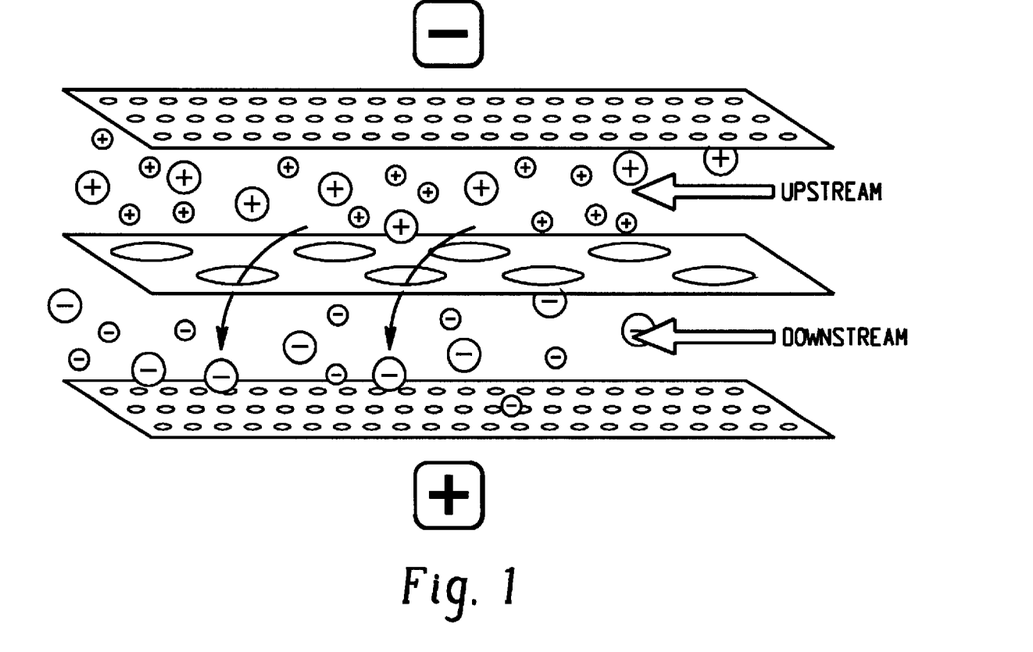
FIG. 1 schematically illustrates an example of charge based separation.

Thus in a solution with a pH between the two pIs, one molecule will have a positive charge, and will tend to move towards the cathode and tend to be contained in the upstream. The other molecule will have a negative charge and will tend to be contained in the downstream as it will tend to move towards the anode. FIG. 1 illustrates an example of charge based separation.

2. Sized Based Separation

Figure 2:
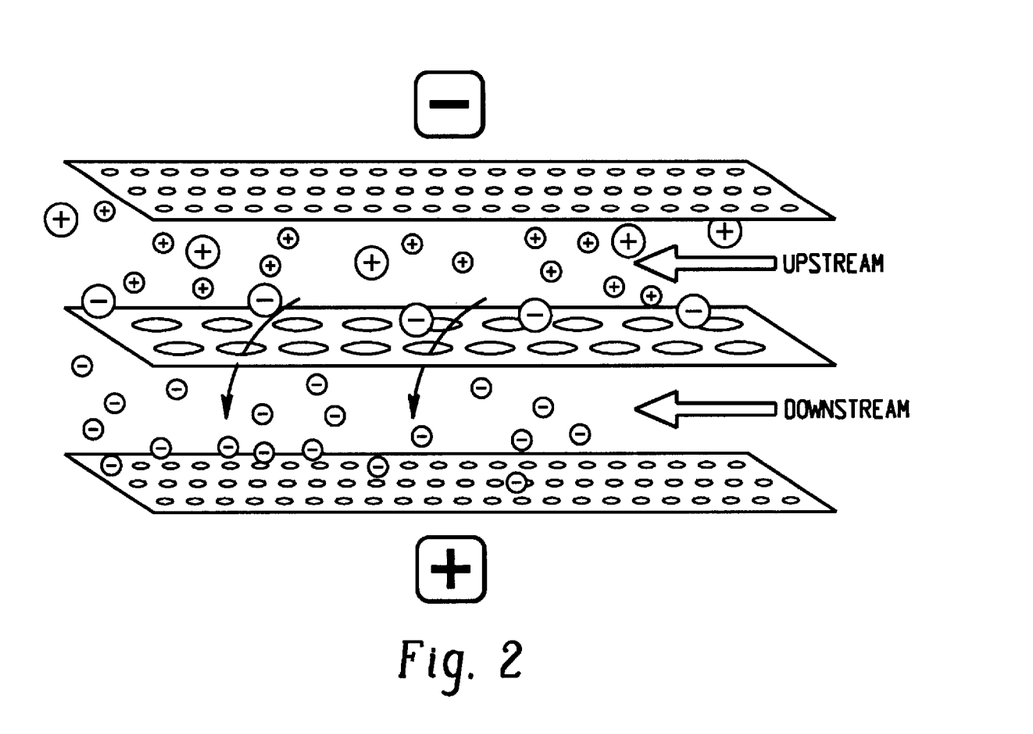
FIG. 2 schematically illustrates an example of size based separation.

Components with different molecular weights may be separated on the basis of pore size. FIG. 2 shows a mode of separation based on size. Two proteins which are both negatively charged, may be separated because the larger molecules tend to be unable to migrate through the smaller pores of the separation membrane. Careful combination of pore size and pH may often allow the isolation of a single component from a complex mixture in one run. (Examples are Mab from ascitic fluid and ovalbumin, lysozyne, or avidin from egg white, and fibrinogen from plasma).

3. Concentration

Figure 3:
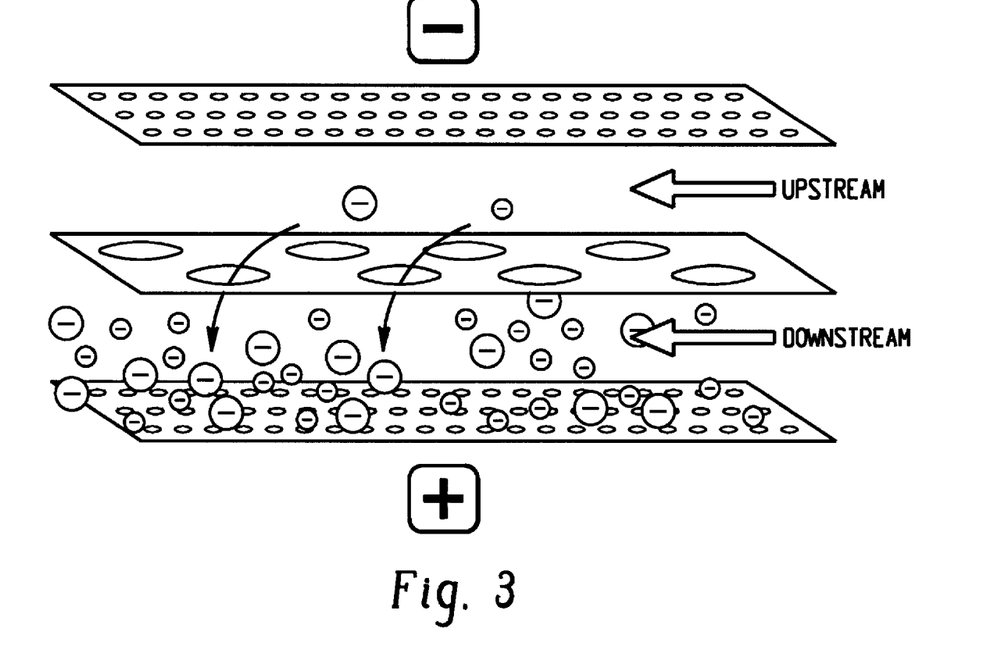
FIG. 3 illustrates an example of concentration.

FIG. 3 illustrates an example of concentration, which tends to utilise a relatively large pore size separation membrane (1,000 kDa). The relatively large pore sizes may enable the rapid transportation of proteins across the separation membrane from a large volume upstream solution to a small volume downstream solution. In this process a pH may be selected in which all of the desired proteins will tend to have the same charge. Typically, pH 8.3 is selected since most proteins will have a negative charge at this pH. In many applications, purification may be achieved at the same time as concentration.

4. Dialysis

Figure 4:
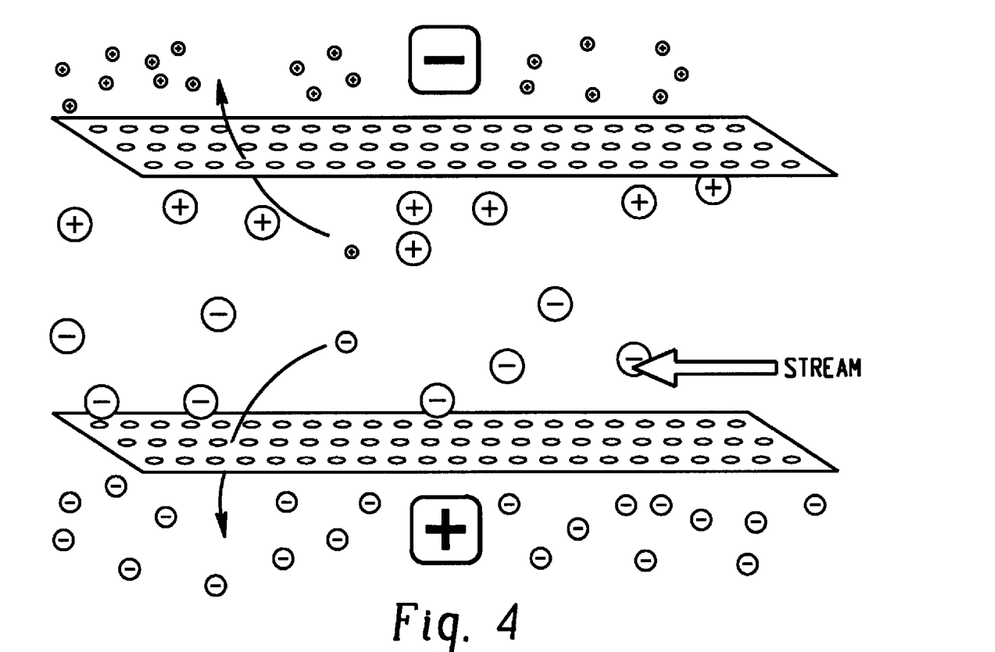
FIG. 4 illustrates an example of dialysis.

FIG. 4 illustrates an example of dialysis. The apparatus in accordance with the present invention may be operated for desalting. The separation membrane is not necessary for dialysis, which can be performed with or without this membrane. The ions may be removed from the sample by passing through the restriction membranes and they then tend to be washed away by the outer buffer streams. This process may also occur during standard fractionation or concentration, but in these cases the ions are usually recirculated. When being used for extensive dialysis, the outer buffer, where the ions collect, should preferably be exchanged for fresh buffer solution at regular intervals.

Figure 5:
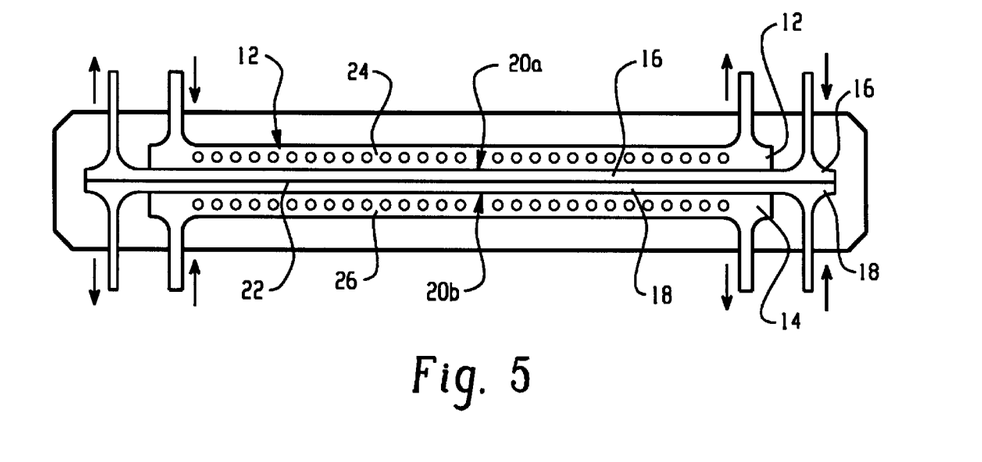
FIG. 5 is a schematic diagram of a separation unit in accordance with an embodiment of the present invention.

Having outlined some of the principals of operation of an apparatus in accordance with the present invention, we now turn to a description of the apparatus itself with reference to FIG. 5 which is a schematic cross-section through an example of a separation unit in accordance with the present invention.

The separation unit may comprise an electrolytic cell which may include four chambers. The two outer chambers 12 and 14 may house the electrodes and a flow of buffer may pass through these chambers. The inner chambers may be called the upstream and downstream channels which may be separated from the outer buffer chambers by restriction membranes 20a, 20b. A separation membrane 22 may separate the upstream and downstream chambers. The upper negative electrode 24 may be referred to as the cathode and the lower positive electrode 26 may be referred to as the anode.

Figure 6:
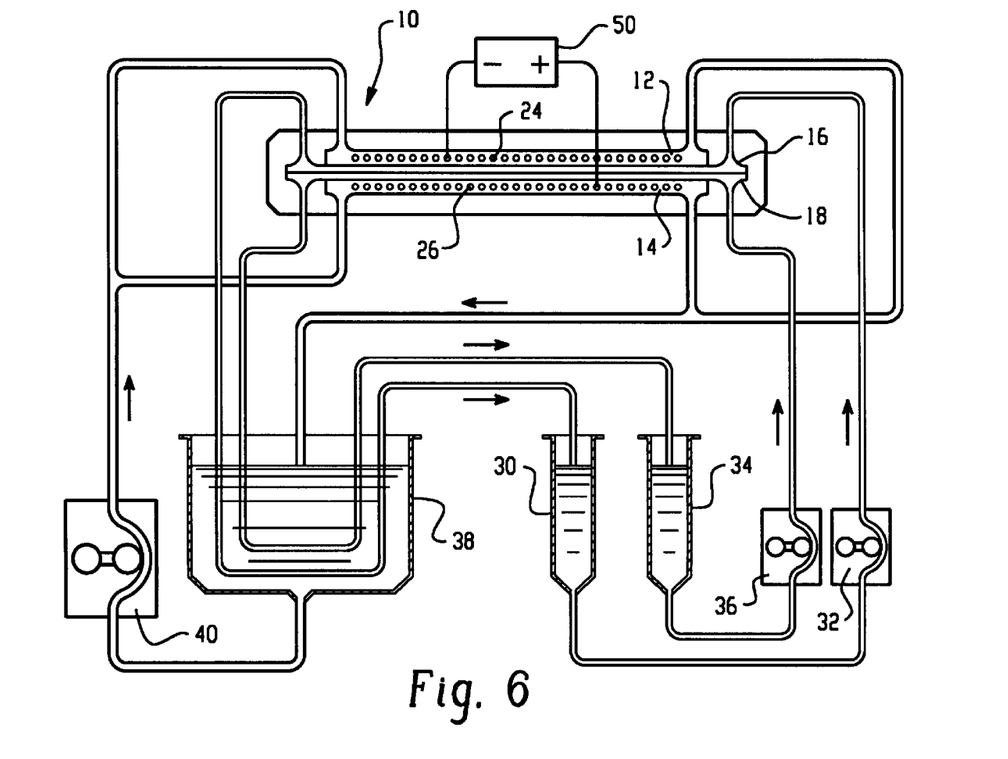
FIG. 6 is a schematic diagram of an apparatus in accordance with an embodiment of the present invention which includes the separation unit of FIG. 5.

A schematic diagram of an exemplary embodiment of an apparatus in accordance with the present invention is shown in FIG. 6. As shown in the illustrative example, the four chambers 12 to 18 are connected to three flow circuits. Each flow circuit may consist of a reservoir and a circulating pump. Thus the upstream reservoir may comprise upstream reservoir 30 and pump 32 and associated tubing, the downstream circuit may comprise downstream reservoir 34, pump 36 and associated tubing and the buffer circuits may share a single buffer reservoir 38 and a single buffer pump 40. The circuit may divide into two paths prior to passing through the two buffer chambers 12 and 14 and after passing through the chambers, the two paths may rejoin.

The separation unit may be cooled by various means such as ice bricks or cooling coils (external apparatus) placed in the buffer reservoir to control its temperature, or by any other suitable cooling means. The upstream and downstream reservoir flow paths tend to pass through the buffer reservoir and heat may be exchanged between the upstream and the buffer reservoir, and the downstream and the buffer reservoir. This heat exchange tends to maintain a low temperature in the upstream and downstream, which is preferred for protein separation.

In the purely illustrative embodiment described above, the buffer pump 40 may be incorporated into the apparatus. The pumps 32 and 36 for the upstream and downstream may be external or internal.

The electrodes may be connected to an external power supply 50 via electrical connecting leads. The power supply may ideally have a variable voltage up to 200 V at and may be capable of delivering up to one amp. Relatively higher voltages, up to 500 V may be used provided that the total power (voltage x current) is maintained at less than about 200W.

The buffer solution provides the ions which may provide the current flow in the electrolytic cell. The buffer also tends to stabilise the pH during separation and to act as the cooling medium. The buffer flow may also help prevent build up of gases at the electrodes generated by electrolysis.

Figure 7:
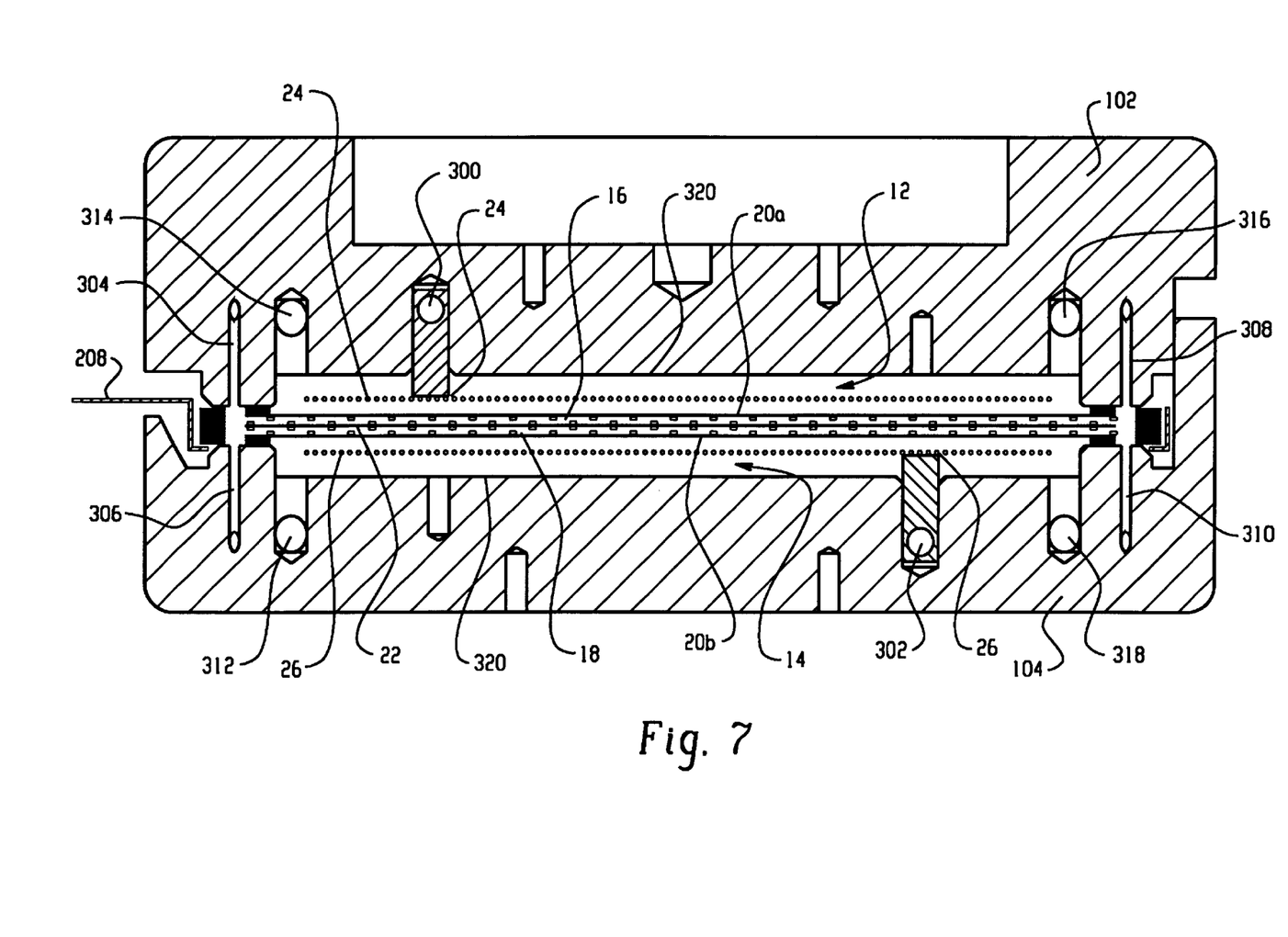
FIG. 7 is a section through a clamp means which forms part of an apparatus in accordance with an embodiment of the present invention.
Figure 8:
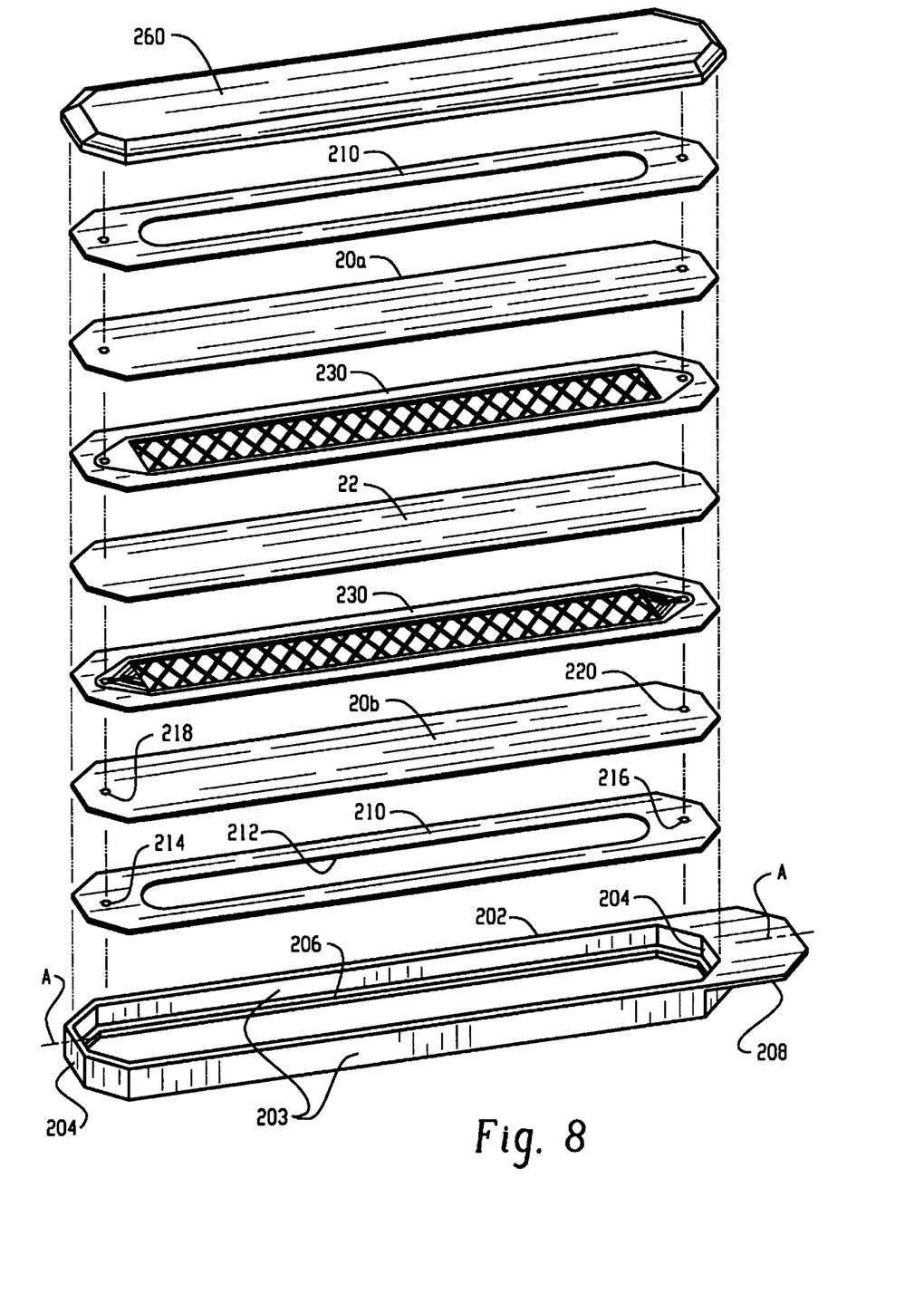
FIG. 8 is a exploded view of a cartridge which may be used with an embodiment of the present invention

FIG. 7 shows an example of a separation unit housing a cartridge (or cassette) and FIG. 8 shows an exploded view of the cartridge of FIG. 7. The separation unit may include an upper connection block 102 and a lower connection block 104 between which, in use, the cartridge may be clamped.

The cartridge may comprise a cartridge housing 202 which may hold the components of the cartridge. The cartridge may be generally elongate and may include two parallel elongate side walls 203 which may extend along the longitudinal axis A—A of the cartridge. Each end of the cartridge may include three end walls so that the cartridge may be generally octagonal in plan view. A small flange 206 may extend around the base of the walls 203, 204. The flange may project inwards towards the centre of the cartridge. On the right hand side of the cartridge, as oriented in FIG. 8 a flap 208 may be provided which may act as a handle for holding or manipulating the cartridge. A planar silicon rubber gasket 210 whose exterior is generally octagonal may be configured to fit inside the walls on the cartridge resting on the flange 206. The centre of the gasket may define an elongate cut out portion 212. Adjacent either end of the seal a small cylindrical hole 214, 216 may be provided.

Above the gasket 210 a first restriction membrane 20b may be located. The external shape of the gasket may be generally the same as that of the interior of the cartridge so that it too may fit inside the cartridge. The membrane may have two holes 218, 220 adjacent either end of the membrane and positioned so that when the cartridge is assembled, those holes tend to align with the holes 214, 216 of the gasket 210. The restriction membrane may typically be formed from a thin substrate and coated with compounds to give a relatively small pore size, such as polyacrylamide gel, so that only very small particles such as ions tend to pass through the gel. Such pores tend to be too small to allow the passage of macromolecules such as proteins.

Above the restriction membrane there may be a first grid element 230. Above that grid element 230 the separation membrane 22 is located. The pore size of the separation membrane used may depend on the size of the particular molecules being separated and the actual mode of separation being used.

Figure 11:
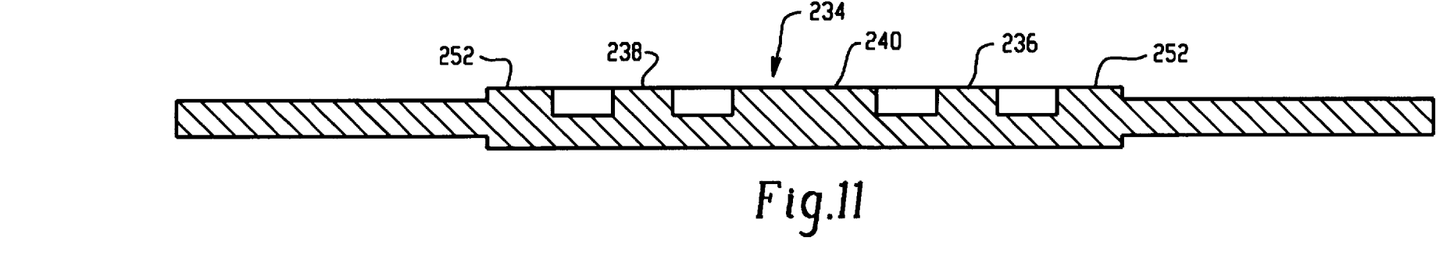
FIG. 11 is a cross-section on lines XI—XI of FIG. 9A
Figure 12:
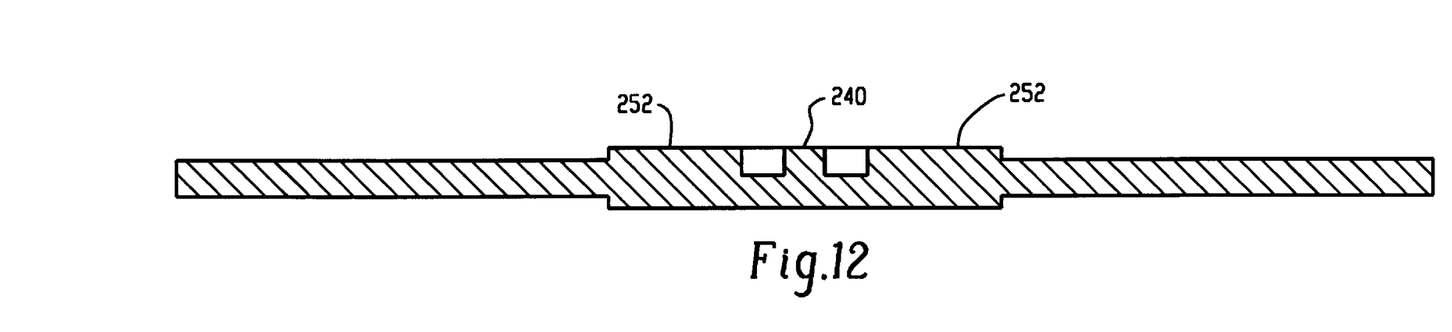
FIG. 12 is a cross-section on lines XII—XII of FIG. 9A.

One function of the grid element 230 is to tend to keep membranes 20a and 22 apart. The grid element also may provide a flow path for the upstream (or the downstream, since the grid elements for both may be identical). The grid element may be generally planar and the exterior of the grid element may be shaped to fit inside the walls of the cartridge housing. An example of a grid element in accordance with the present invention is shown in more detail in FIGS. 9 through 12. An elongate rectangular cut-out portion 231 which incorporates lattice work may be defined in the centre of the grid element. At each end of the grid a through hole 232 may be provided, which in the assembled cartridge, may be aligned with holes 214 and 218 of the gasket and restriction membrane, respectively. A triangular channel area 234 having sides and a base, may extend and diverge from the hole to the cut out portion 231. Upstanding ribs 236, 238, 240, best seen in FIGS. 11 and 12, may be defined in the channel area 234. Liquid flowing up through the hole 232 may thus pass along the triangular channel area 234 between the ribs and into the lattice. The ribs may direct the flow from the hole 232 and tend to ensure that the liquid is evenly distributed along the cross-section of the lattice. The ribs may also provide support to the separation membrane 22 disposed above the grid element. The narrow channels defined by the ribs also tend to increase the liquid velocity and pressure in the downstream.

The lattice may comprises a first array of spaced parallel members 241 extending at 45° to the longitudinal axis of the grid disposed above and integrally formed with a second lower set of spaced parallel members 242 extending at 90° to the first set of members. As illustrated in the example shown in FIG. 10, the upper and lower surfaces of the members may be rounded. The absence of any sharp edges helps prevent damage to the separation membrane 22. Further, any increased pressure on the separation membrane 22 will tend to increase the area of contact between the curved lattice members and the separation membrane and may thus provide extra support to the separation membrane. The lattice may evenly distribute the flow of liquid over the separation membrane surface. The use of a first set of members disposed above a second set of members tends to ensure that the liquid in the downstream is forced to move up and down and change direction frequently and this helps to encourage mixing of the liquid and tends to inhibit static flow zones.

Figure 9A:
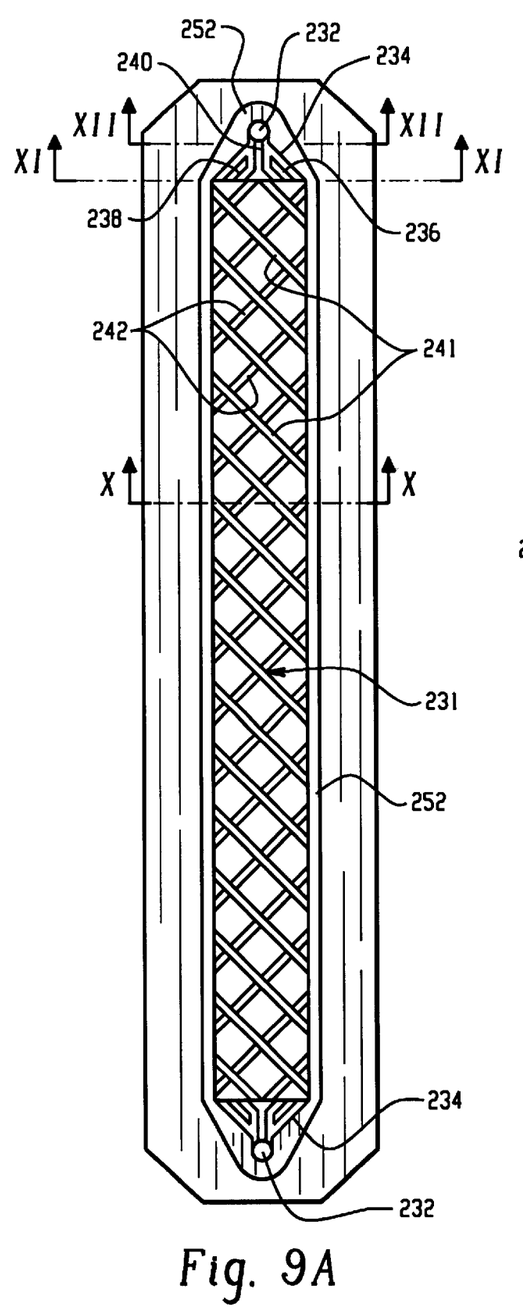
FIG. 9A is a plan view of a grid element which may be a component of the cartridge of FIG. 8.
Figure 9B:
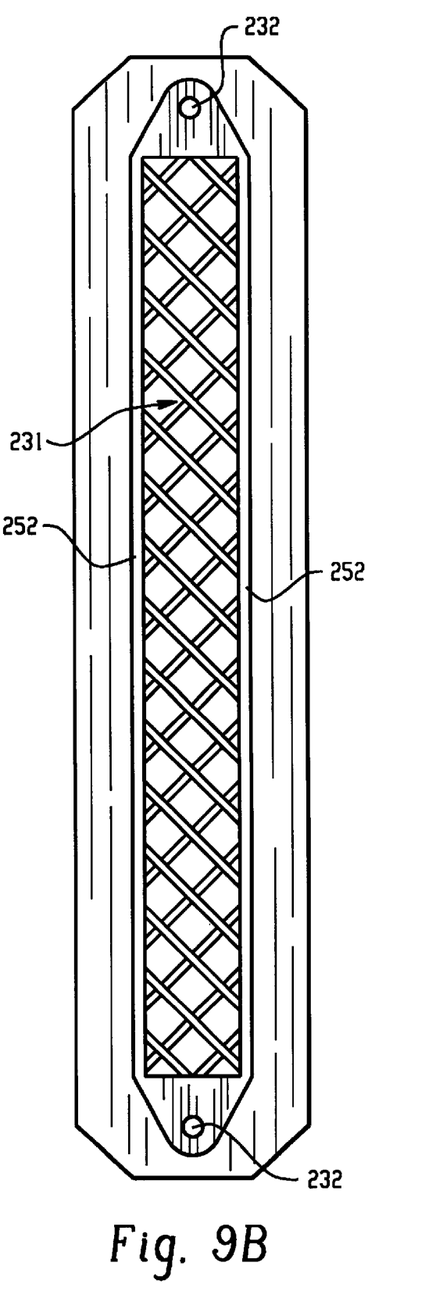
FIG. 9B is a reverse plan view of the grid element of FIG. 9A

The reverse side of the grid element as illustrated in FIG. 9B may be relatively smooth and flat aside from the cut-out 231 and the holes 232, which tends to ensure sealing between the buffer stream and the downstream.

Figure 10:
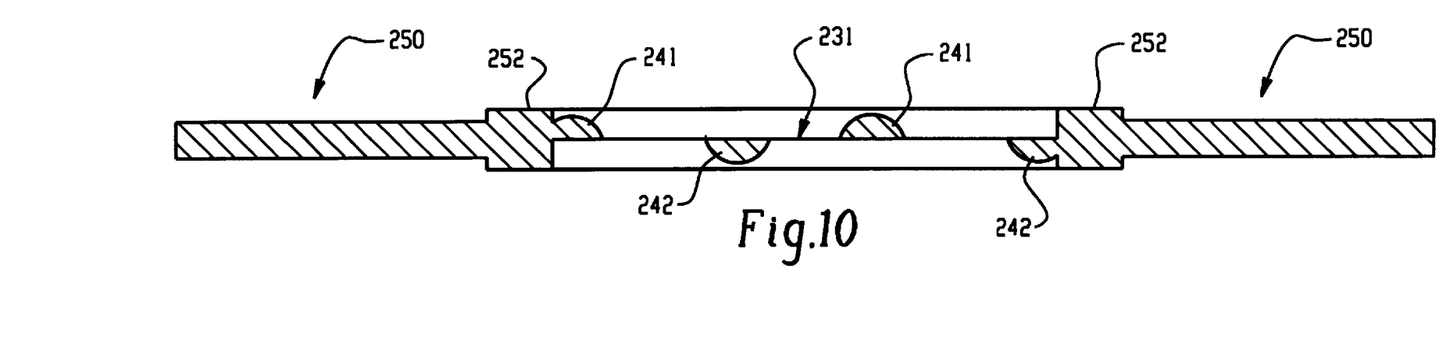
FIG. 10 is a cross-section on lines X—X of FIG. 9A.

The thickness of the grid element may be relatively small. With reference to FIG. 10, the exterior areas of the element may be 0.8 mm thick. A sealing rib or ridge 252 may extend around the periphery of the grid to improve sealing. The ridge may be 1.2 mm thick measured from one side of the grid element to the other. The distance between opposite peaks of the lattice elements 241, 242 measured from one side of the grid to the other may be 1 mm. The relative thinness of the grid may provide several advantages. First, a relatively thin grid element tends to increase the liquid velocity and pressure and thus may result in a more even distribution of liquid over the separation membrane 22. The resultant relatively higher liquid velocity may also assist in inhibiting fouling of the separation membrane 22. Fouling may occur when macromolecules block the pores of the separation membrane or stick to the separation membrane.

Also, the volume of liquid required may be decreased by the use of a relatively thin grid which enables relatively smaller sample volumes to be used for laboratory separations and this may be a significant advantage over the prior art when the samples are expensive to produce.

Finally, the use of a relatively thinner grid element may enable less electrical power to be deposited into the liquid since power supplied to the liquid across the grid region, depends on the thickness of the grid. Thus, a relatively smaller power supply unit may be used, and this may make the process more economical. If less heat is transferred into the liquid the temperature of the liquid remains lower. This is advantageous since high temperatures may destroy the sample and product.

The separation membrane 22 may be selected depending on the application as discussed earlier in the description relating to FIGS. 1 to 4 of the drawings. Following the separation membrane there may be a mirror image of elements 210, 220: there is a further grid element 230, a restriction membrane 20a, and a further gasket 210 which may be symmetrically arranged about the separation membrane 22. Those three components may form the upstream and a part of the boundary of the buffer stream. The components may be held in the cartridge 200 by means of a clip 260 which may be snap fitted or glued around the top of the walls 204 of the cartridge.

One function of the cartridge is to hold the components together for insertion into the separation unit. The actual cartridge walls tend to have no effect on the sealing of the system. In accordance with one embodiment of the invention the system may be sealed in manner in which no liquid contacts the walls of the cartridge in use.

FIG. 7 illustrates an example of a cartridge located in the clamping unit between connecting blocks or jaws 102 and 104. The jaws may house the inlets and outlets for feeding buffer flows, a downstream and an upstream into the cartridge. The jaws may include inlets 304 and 306 which respectively may allow the upstream and downstream flows into the grid via the holes 214,216,230. Outlets 308 and 310 may be similarly provided. Inlets 312 and 314 and outlets 316 and 318 may feed buffer past the restriction membranes 20a, 20b along the flow path defined between a recess or channel 320 in the lower jaw 104 in which the anode may be located, and the gasket 210 and the restriction membrane 20b. A similar arrangement may be provided in the upper jaw which may house the cathode. The jaws may be mounted between a simple screw clamp unit so that a simple screw operated knob may be used to open and close the jaws for changing the membrane cartridge.

The electrodes 26, 24 may be formed from platinum coated titanium expanded mesh, in contrast with the standard electrodes usually used for electrolytic cells which comprise platinum wire. The platinum coated titanium expanded mesh used in the apparatus of the present invention has several advantages over platinum wire in particular the ridged structure is self supporting and less expensive than platinum wire. The mesh also may provide a greater surface area and tends to allow higher currents to pass through the separation unit with less electrical power losses of the electrode. The electrodes may thus have a longer useful life.

Finally, the larger surface area distributed over the buffer channel may provide a more even electrical field for the separation process.

The electrodes may also be located relatively close to the restriction membranes.

This tends to enable less electrical power to be used and deposited into the buffer liquid and consequently less heating of the buffer liquid may occur. Connectors 300 and 302 from the electrodes may pass to sockets for connection of electrical power to the electrodes. The electrodes may be shrouded to prevent accidental contact with an operators fingers or the like.

In use, a cartridge in accordance with the present invention may be loaded into the apparatus, the jaws may be closed to seal the components in place, the buffer solution and upstream and downstream may be fed through the connection blocks and thence through the cartridge and the apparatus may be connected to a power supply. The electrical power may be set to the desired value and separation may be carried out using one of the modes described earlier with reference to FIGS. 1 to 4. After the separation has been carried out, the used cartridge may simply be removed and replaced with another cartridge ready for re-use. The upstream and downstream sample circuits may be cleaned and the buffer replaced if necessary. Following that the apparatus is ready to carry out a further separation.

Figure 13:
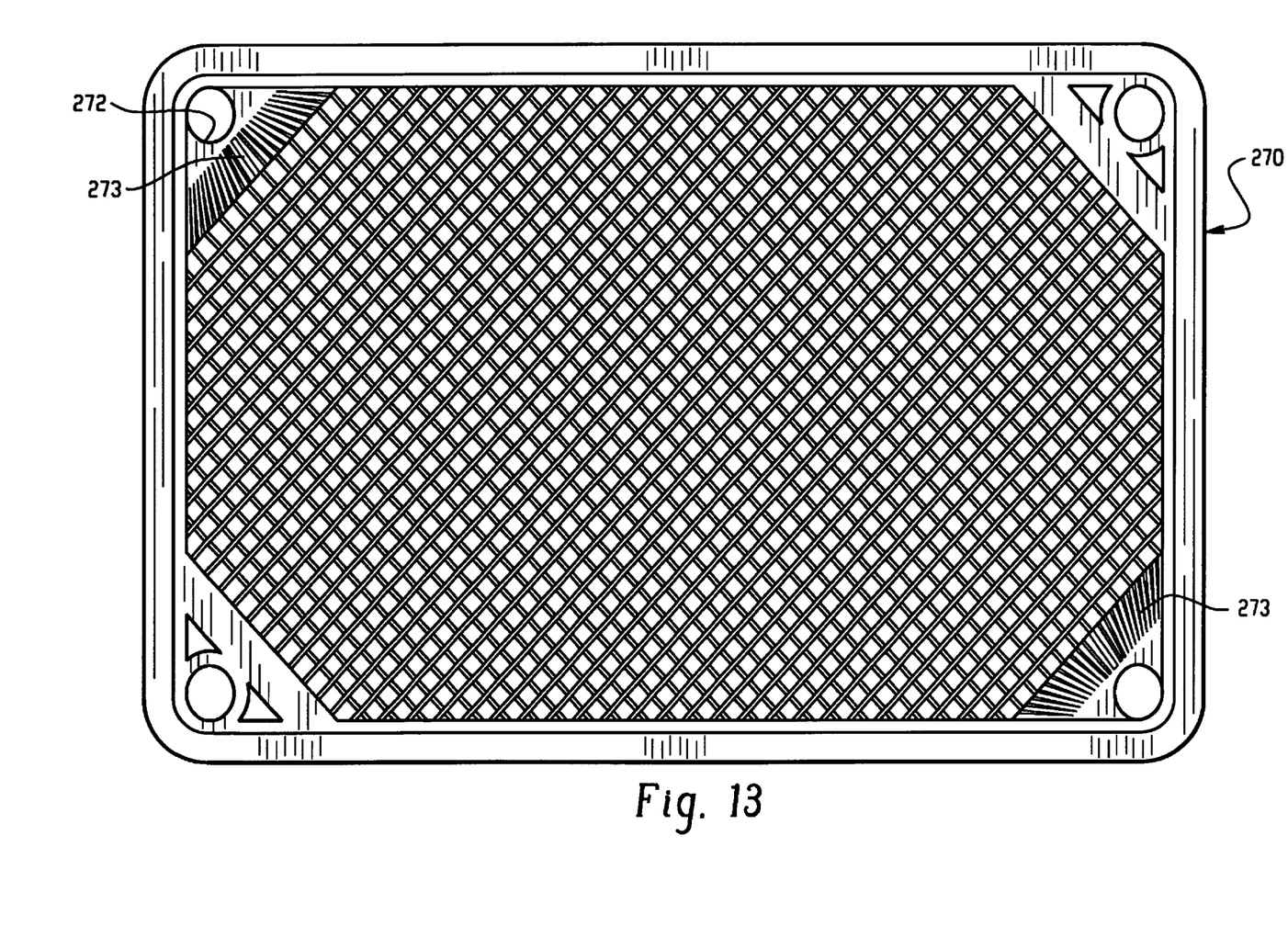
FIG. 13 is a plan view of a grid element which may be used with a second embodiment of the present invention.

FIG. 13 illustrates a grid element 270 for a second embodiment of the present invention which utilises a separation membrane having a much larger surface area than that of grid element 230. The principal of operation of this grid element may be generally the same as that of the smaller grid element 230 although the holes 272 through which the downstream or upstream is fed are located in two of the comers of the grid element and there may be more channels 273 feeding the streams from the holes 272 to the central portion 274 of the grid. The cartridge, casing and other components of the cartridge may also be relatively increased in area so that they have approximately the same area as the grid.

What is claimed is:

1. An electrophoresis apparatus, comprising:
   a cartridge configured to be removably mounted in the apparatus;
   at least one separation membrane positioned in the cartridge, the at least one separation membrane having a first side along which a first flow path is provided and a second side along which a second flow path is provided;
   a plurality of restriction membranes for separating buffer flow from the first flow path and the second flow path whereby the cartridge is removable from the apparatus for replacement with another cartridge;
   an upper connection block and a lower connection block wherein the upper connection block and lower connection defines inlet and outlet means for feeding liquid into the first flow path and the lower connection block defines inlet and outlet means for feeding liquid into the second flow path;
       wherein the upper connection block house electrodes and connection means for connecting the electrodes to a power source; and
           wherein the electrodes comprise titanium mesh coated with platinum.

2. An electrophoresis apparatus comprising:
   a cartridge configured to be removably mounted in the apparatus;
   at least one separation membrane positioned in the cartridge, the at least one separation membrane having a first side along which a first flow path is provided a second side along which a second flow path is provided;
   a plurality of restriction membranes for separating buffer flow from the first flow path and the second flow path whereby the cartridge is removable from the apparatus for replacement with another cartridge; and
   an upper connection block and a lower connection block wherein the upper connection block and lower connection defines inlet and outlet means for feeding liquid into the first flow path and the lower connection block defines inlet and outlet means for feeding liquid into the second flow path;
       wherein the upper connection block house electrodes and connection means for connecting the electrodes to a power source; and
       wherein the upper electrode is housed in a first channel defined in the upper connection block and the lower electrode is housed in a second channel defined in the lower connection block, said first channels defining a part of a boundary of a first buffer flow path for the apparatus and wherein an other part of that boundary for the first buffer flow path is defined by one of the restriction membranes housed in the cartridge.

3. An electrophoresis apparatus comprising:
   a cartridge configured to be removably mounted in the apparatus;
   at least one separation membrane positioned in the cartridge, the at least one separation membrane having a first side along which a first flow path is provided and second side along which a second flow path is provided;
   a plurality of restriction membranes for separating buffer flow from the first flow path and the second flow path whereby the cartridge is removable from the apparatus for replacement with another cartridge; and
   an upper connection block and a lower connection block wherein the upper connection block and lower connection defines inlet and outlet means for feeding liquid into the first flow path and the lower connection block defines inlet and outlet means for feeding liquid into the second flow path;
       wherein the upper connection block and the lower connection block comprise a plastics material; and
       wherein the upper electrode is housed in a first channel defined in the upper connection block and the lower electrode is housed in a second channel defined in the lower connection block, said first channels defining a part of a boundary of a first buffer flow path for the apparatus and wherein an other part of that boundary for the first buffer flow path is defined by one of the restriction membranes housed in the cartridge.

4. An electrophoresis apparatus comprising:
   a cartridge configured to be removably mounted in the apparatus;
   at least one separation membrane positioned in the cartridge, the at least one separation membrane having a first side along which a first flow path is provided and a second side along which a second flow path is provided;
   a plurality of restriction membranes for separating buffer flow from the first flow path and the second flow path whereby the cartridge is removable from the apparatus for replacement with another cartridge; and
   an upper connection block and a lower connection block wherein the upper connection block and lower connection defines inlet and outlet means for feeding liquid into the first flow path and the lower connection block defines inlet and outlet means for feeding liquid into the second flow path;

wherein the electrodes comprise titanium mesh coated with platinum; and wherein the upper electrode is housed in a first channel defined in the upper connection block and the lower electrode is housed in a second channel defined in the lower connection block, said first channels defining a part of a boundary of a first buffer flow path for the apparatus and wherein an other part of that boundary for the first buffer flow path is defined by one of the restriction membranes housed in the cartridge.

5. An electrophoresis apparatus as comprising:

a cartridge configured to be removably mounted in the apparatus;

at least one separation membrane positioned in the cartridge, the at least one separation membrane having a first side along which a first flow path is provided and a second side along which a second flow path is provided;

a plurality of restriction membranes for separating buffer flow from the first flow path and the second flow path whereby the cartridge is removable from the apparatus for replacement with another cartridge; and an upper connection block and a lower connection block wherein the upper connection block and lower connection defines inlet and outlet means for feeding liquid into the first flow path and the lower connection block defines inlet and outlet means for feeding liquid into the second flow path;

wherein the upper connection block defines an inlet and an outlet for a first buffer flow path and the lower connection block defines an inlet and an outlet for a second buffer flow path; and wherein the upper electrode is housed in a first channel defined in the upper connection block and the lower electrode is housed in a second channel defined in the lower connection block, said first channels defining a part of a boundary of a first buffer flow path for the apparatus and wherein an other part of that boundary for the first buffer flow path is defined by one of the restriction membranes housed in the cartridge.

\* \* \* \* \*